(12) United States Patent
Papavassiliou et al.

(10) Patent No.: US 11,807,597 B2
(45) Date of Patent: Nov. 7, 2023

(54) METHODS AND SYSTEMS FOR PRODUCING ACETIC ACID

(71) Applicant: LyondellBasell Acetyls, LLC, Houston, TX (US)

(72) Inventors: Vasilis Papavassiliou, Houston, TX (US); Noel C. Hallinan, Loveland, OH (US); David L. Ramage, Friendswood, TX (US); Gary A. Sawyer, Media, PA (US); Rene Zamarripa, Friendswood, TX (US); Michael E. Fitzpatrick, League City, TX (US); Brian A. Salisbury, Beach City, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 70 days.

(21) Appl. No.: 17/710,392

(22) Filed: Mar. 31, 2022

(65) Prior Publication Data
US 2022/0315516 A1 Oct. 6, 2022

Related U.S. Application Data

(60) Provisional application No. 63/170,283, filed on Apr. 2, 2021.

(51) Int. Cl.
| | |
|---|---|
| *C07C 51/12* | (2006.01) |
| *B01J 19/00* | (2006.01) |
| *B01J 19/24* | (2006.01) |
| *B01J 23/46* | (2006.01) |
| *C07C 51/44* | (2006.01) |
| *C07C 51/50* | (2006.01) |

(52) U.S. Cl.
CPC ............ *C07C 51/12* (2013.01); *B01J 19/0013* (2013.01); *B01J 19/2465* (2013.01); *B01J 23/464* (2013.01); *C07C 51/445* (2013.01); *C07C 51/50* (2013.01)

(58) Field of Classification Search
CPC .. B01J 19/0013; B01J 19/2465; B01J 23/464; C07C 51/12; C07C 51/445; C07C 51/50; C07C 51/09; C07C 53/08
See application file for complete search history.

(56) References Cited

U.S. PATENT DOCUMENTS

| | | | |
|---|---|---|---|
| 5,374,774 A | 12/1994 | Ochiai | |
| 5,672,744 A | 9/1997 | Kagotani et al. | |
| 5,817,869 A | 10/1998 | Hinnenkamp et al. | |
| 5,932,764 A * | 8/1999 | Morris ................... | C07C 51/12 562/519 |
| 6,552,221 B1 | 4/2003 | Hallinan et al. | |
| 8,168,822 B2 | 5/2012 | Scates | |
| 8,394,988 B2 | 3/2013 | Torrence et al. | |

(Continued)

OTHER PUBLICATIONS

The International Search Report and The Written Opinion for PCT/US2022/022856 dated Aug. 23, 2022.

*Primary Examiner* — Yevgeny Valenrod
*Assistant Examiner* — Blaine G Doletski (57) ABSTRACT

Methods and systems for producing acetic acid, including glacial acetic acid. A first stream of a reactor fluid that includes methyl acetate, water, and a first amount of carbon monoxide may be forwarded from a reactor to a reactor cooler to form a cooled reactor fluid. The cooled reactor fluid may have a concentration of methyl acetate that is lower than the concentration of methyl acetate in the reactor fluid.

20 Claims, 4 Drawing Sheets

(56) References Cited

U.S. PATENT DOCUMENTS

| | | | |
|---|---|---|---|
| 8,530,696 B2* | 9/2013 | Zinobile | C07C 51/12 |
| | | | 562/517 |
| 8,637,699 B2 | 1/2014 | Hallinan et al. | |
| 9,663,437 B2 | 5/2017 | Torrence et al. | |
| 9,790,159 B2 | 10/2017 | Hallinan et al. | |
| 10,067,113 B2 | 9/2018 | Hallinan et al. | |
| 2015/0246866 A1* | 9/2015 | Hallinan | G01N 33/20 |
| | | | 436/73 |

* cited by examiner

Figure 1.

$$CH_3OH + HI \rightleftharpoons CH_3I + H_2O \quad (A)$$

$$[Rh(CO)_2I_2]^- + CH_3I \longrightarrow [CH_3Rh(CO)_2I_3]^- \quad (B)$$

$$[CH_3Rh(CO)_2I_3]^- + CO \longrightarrow [CH_3C(O)Rh(CO)_2I_3]^- \quad (C)$$

$$[CH_3C(O)Rh(CO)_2I_3]^- \longrightarrow CH_3C(O)I + [Rh(CO)_2I_2]^- \quad (D)$$

$$CH_3C(O)I + H_2O \longrightarrow CH_3C(O)OH + HI \quad (E)$$

$$H_2O + CO \rightleftharpoons CO_2 + H_2 \quad (F)$$

$$CH_3C(O)OH + CH_3OH \longrightarrow CH_3C(O)OCH_3 \quad (G)$$

$$CH_3C(O)OCH_3 + HI \longrightarrow CH_3C(O)OH + CH_3I \quad (H)$$

METHODS AND SYSTEMS FOR PRODUCING ACETIC ACID

PRIOR RELATED APPLICATIONS

This application claims the benefit of priority to U.S. Provisional Patent Application No. 63/170,283, filed on Apr. 2, 2021, which is incorporated herein by reference in its entirely.

FIELD OF THE INVENTION

This invention generally relates to methods and systems for producing acetic acid.

BACKGROUND

Known methods of producing acetic acid (HOAc) include continuously reacting carbon monoxide (CO) and methanol (MeOH) and/or methyl acetate (MeAc) in an unstirred liquid filled reactor. Generally, methanol reacts with acetic acid to produce methyl acetate, which further reacts with CO to form acetic acid. While the reaction per se can be represented by $$CH_3OH + CO \rightarrow CH_3COOH$$

the underlying chemistry is intricate and involves a multiplicity of interrelated reactions, by-products, and equilibria. To be practicable, a manufacturing process, therefore has to balance those reactions, the associated by-products, and the purification of the product. The reaction is exothermic and heat removal is a part of the process design. Examples of known processes are described at U.S. Pat. Nos. 6,552,221; 8,637,699; and 10,067,113, which are incorporated herein by reference.

There are a number of known additives that may be used in processes for producing glacial acetic acid. For example, U.S. Pat. No. 9,790,159 discloses additives selected from pentavalent alkyl phosphine oxides that demonstrate reactor stability at reactor water concentrations of less than 2 wt % in a pilot unit. Previously known additives, such as triphenylphosphine oxide, were typically limited to operation at >6 wt % water in a reactor.

Most of the heat of reaction for methanol carbonylation is currently removed by flash vaporization. Reactor fluid is circulated to the flash tank at low pressure, where vaporization provides the feed to a light ends column, and the cooled liquid is pumped back to the reactor. This flashed vapor carries with it about 0.726 kg (1.6 pounds) of acid for every 0.454 kg (1 pound) of glacial acetic acid (GAA) product. That is, about 0.272 kg (0.6 pounds) of acid are processed through the back-end distillation train and recycled to the reactor, for every 0.454 kg (1 pound) of GAA product. This recycle also includes other components like methyl iodide, water, and methyl acetate that are flashed with the acid.

Reducing the acid recycle to the reactor may allow the feed rate of reactants to be increased, thereby possibly improving the reactor production rate by 10-100% or more. However, this can create two operating problems for the reactor. A first problem is that increasing the reaction rate increases the need to remove the additional heat of reaction. A second concern is the concentration of MeAc in the reactor which is preferably maintained at 5% or less. Increased MeAc concentrations in the reactor can lead to lower heavy phase density in a decanter, which could lead to loss of phase separation in the decanter, plant shut downs, and/or production disruptions. An increased feed rate of reactants, without other process changes, can lead to an increased concentration of MeAc. While increasing the reactor temperature, increasing the catalyst concentration, and/or decreasing the feed rate may serve to decrease methyl acetate concentration, each usually is associated with an energy cost, a material cost, and/or a production decrease.

There remains a need for methods and systems that address one or more problems caused by heat surplus and/or high MeAc concentration.

BRIEF SUMMARY

Provided herein are methods that may include controlling reactor cooling and reactor MeAc concentration with a reactor cooler. Also provided are systems, embodiments of which include a reactor cooler that provides reactor cooling and controls reactor MeAc concentration. The methods and systems described herein may allow a target steady state reactor MeAc concentration to be maintained at a higher feed rate, a lower catalyst and/or methyl iodide (MeI) concentration, or a combination thereof, thereby potentially allowing higher throughput through the reaction section of a system. In some embodiments, the methods and systems described herein permit an increase in acetic acid production to be achieved by incorporating a reactor cooler described herein into known systems and methods.

In one aspect, methods for producing acetic acid, including glacial acetic acid, are provided. In some embodiments, the methods include contacting a first amount of carbon monoxide with a reactor fluid, in a reactor, in the presence of a carbonylation catalyst, the reactor fluid including iodide, less than or equal to 6 wt % water based on the total weight of the reactor fluid, and one or more additives, in-situ generated derivatives of the one or more additives, or combinations thereof at an additive to iodide molar ratio of 0.5:1 to 5:1, under carbonylation conditions sufficient to form acetic acid and an intermediate reaction product comprising methyl acetate, the reactor fluid having a first concentration of methyl acetate, wherein the one or more additives include a compound mixture of tri-n-octylphosphine oxide (TOPO), tri-n-hexylphosphine oxide (THPO), dihexylmonooctylphosphine oxide and dioctylmonohexylphosphine oxide; directing a first stream of the reactor fluid from the reactor to a reactor cooler, the first stream having a first concentration of methyl acetate; cooling the portion of the reactor fluid received in the reactor cooler for a residence time sufficient to form a cooled reactor fluid having a second concentration of methyl acetate less than the first concentration of methyl acetate; directing a second stream of the cooled reactor fluid from the reactor cooler to the reactor; contacting a third stream comprising a second amount of carbon monoxide with the first stream; maintaining an acetic acid evaporation rate in the reactor; and recovering acetic acid. In some embodiments, the reactor fluid comprises methanol. In some embodiments, the reactor fluid comprises hydrogen iodide. In some embodiments, the reactor fluid comprises up to 1 wt %, 2 wt %, 3, wt %, 4 wt %, 5 wt %, 6 wt %, 7 wt %, 8 wt %, 9 wt %, or 10 wt % hydrogen iodide based on the total weight of the reactor fluid. In some embodiments, the additive to iodide molar ratio is in the range of 0.5:1 to 5:1. In some embodiments, the additive to iodide molar ratio is in the range of 0.5:1 to 3:1. In some embodiments, the additive to hydrogen iodide molar ratio is in the range of from 0.5:1 to 1.5:1 In some embodiments, the additive to hydrogen iodide molar ratio is in the range of 1:1 to 5:1. In some embodiments, the additive to hydrogen iodide molar ratio is in the range of 1:1 to 2.5:1.

In some embodiments, the additive to hydrogen iodide molar ratio is in the range of 1.5:1 to 4:1. In some embodiments, the acetic acid evaporation rate in the reactor is maintained essentially constant.

In another aspect, systems are provided for producing acetic acid, including glacial acetic acid. In some embodiments, the systems include a reactor including a first outlet and a first inlet through which fluids are forwarded to and returned from, respectively, a reactor cooler which includes a corresponding second inlet and second outlet. The reactor coolers of the systems described herein may be configured to operate at a lower temperature than the reactors, but the temperature of the reactor coolers can be high enough to allow a carbonylation reaction to occur. The system also may include at least one flash tank, a light ends column, a decanter, a drying column, a heavy ends column, a waste aid stripper, or a combination thereof.

Additional aspects will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION OF THE INVENTION

Figure 1:
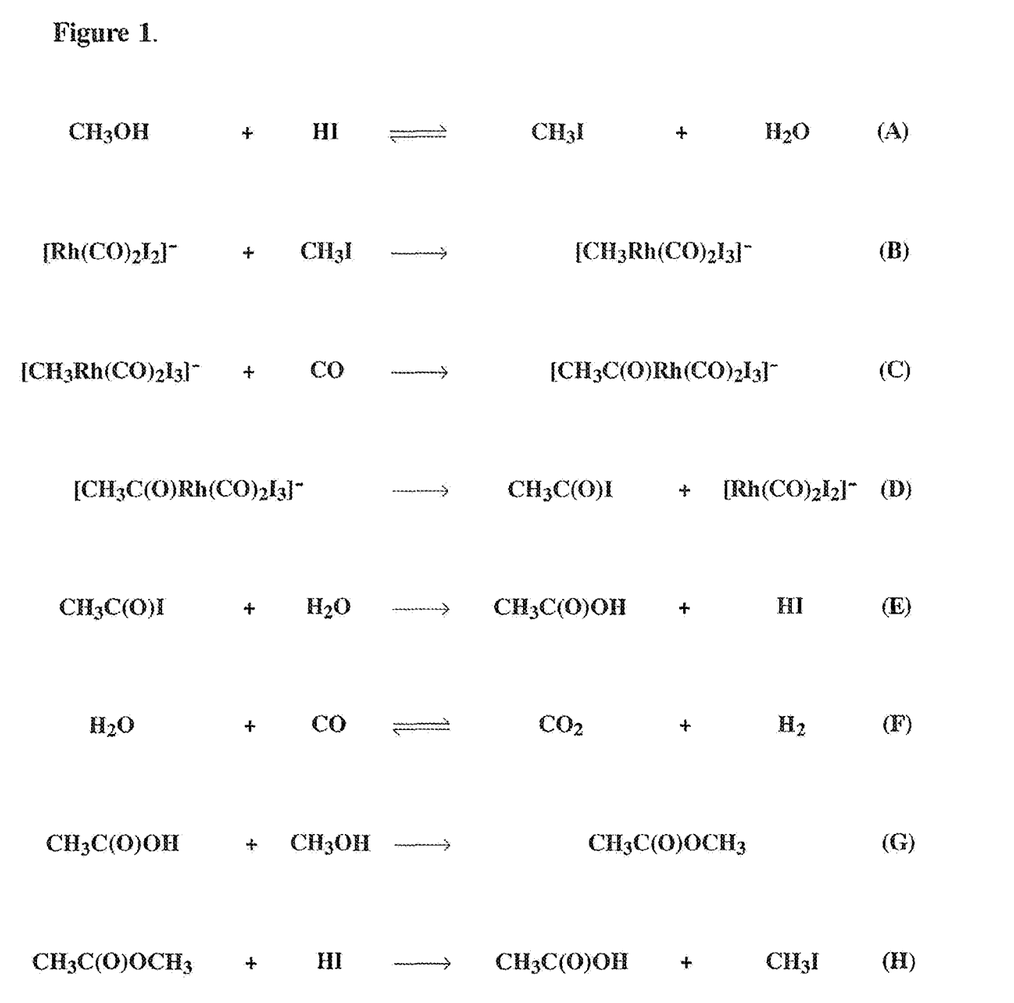
FIG. 1 sets forth some of the interrelated reactions and equilibria believed to be involved in the carbonylation of methanol in the presence of a rhodium catalyst.

FIG. 1 sets forth some of the interrelated reactions and equilibria believed to be involved in the carbonylation of methanol in the presence of a rhodium catalyst. Those of ordinary skill in the particular art will appreciate that further reactions and equilibria are involved and that the reproduced reactions are merely an illustration of the complexity of the multiplicity of interrelated reactions, by-products and equilibria.

Methods are provided for making acetic acid, including glacial acetic acid. In some embodiments, the methods include providing a reactor, a reactor cooler, and a reactor fluid disposed in the reactor.

The reactor may include a first outlet and a first inlet through which fluids are forwarded to and returned from, respectively, the reactor cooler. The reactor cooler, in turn, may include a corresponding second inlet and second outlet. The "corresponding" second inlet of the reactor cooler receives a first stream from the first outlet of the reactor, and the first inlet of the reactor receives a second stream from the "corresponding" second outlet of the reactor cooler.

The reactor fluid generally may include any of the one or more reactants and/or one or more products that may be used or produced, respectively, in the methods for producing acetic acid. In some embodiments, the reactor fluid includes methyl acetate, water, and a first amount of carbon monoxide. One or more components of the reactor fluid may independently be supplied continuously or intermittently through one or more feeds to the reactor. For example, methanol and/or methyl acetate may be added to the reactor via a liquid feed, while carbon monoxide may be introduced to a reactor via a sparger ring. Additionally or alternatively, methyl acetate can be formed in situ. The reactor fluid may also include methanol, which may react quickly upon its addition to the reactor. The reactor fluid also may include a catalyst. The catalyst may be present as part of a soluble catalyst system, as described herein. The reactor fluid also may include one or more additives. The one or more additives may include those described herein which are capable of reducing the amount of water that can be present in a reactor fluid without adversely impacting one or more properties of the reactor fluid, the methods described herein, or a combination thereof.

A pressure may be applied to the reactor. The pressure generally may be applied with any gas that does not undesirably impact the methods described herein. In some embodiments, the methods described herein include applying the pressure with the first amount of carbon monoxide.

In some embodiments, a pressure in the reactor is about 2.413 MPa (350 psig) to about 3.102 MPa (450 psig). In some embodiments, a pressure in the reactor is about 2.413 MPa (350 psig) to about 2.792 MPa (405 psig). In some embodiments, a pressure in the reactor is about 2.654 MPa (385 psig) to about 3.102 MPa (450 psig). In some embodiments, a pressure in the reactor is about 2.586 MPa (375 psig) to about 2.930 MPa (425 psig). In some embodiments, a pressure in the reactor is about 2.654 MPa (385 psig) to about 2.792 MPa (405 psig). In some embodiments, a pressure in the reactor is about 2.689 MPa (390 psig) to about 2.758 MPa (400 psig). In some embodiments, a pressure in the reactor is about 2.723 MPa (395 psig) to about 2.758 MPa (400 psig).

In some embodiments, the methods include forwarding a first stream including the reactor fluid to the reactor cooler to form a cooled reactor fluid. The forwarding of the first stream may be achieved by any techniques known in the art. The first stream may be forwarded through a pipe section that connects the first outlet of the reactor with the second inlet of the reactor cooler. The first stream may have a residence time in the reactor cooler that is effective to form the cooled reactor fluid.

In some embodiments, the methods described herein include contacting the first stream including the reactor fluid, the cooled reactor fluid, or a combination thereof with a third stream including a second amount of carbon monoxide. The contacting of the first stream, the cooled reactor fluid, or a combination thereof with the third stream including a second amount of carbon monoxide may be achieved by any known technique. The third stream that includes carbon monoxide can be a stream that is redirected from a stream of carbon monoxide provided to a reactor, or the third stream may be a separate stream that includes carbon monoxide.

In some embodiments, the contacting of the first stream, the cooled reactor fluid, or a combination thereof with the third stream includes injecting the third stream including a second amount of carbon monoxide into the reactor cooler through a sparger or a supersonic injector. In some embodiments, the contacting of the first stream, the cooled reactor fluid, or a combination thereof with the third stream includes generating bubbles of carbon monoxide in an apparatus that connects the first outlet of the reactor and the second inlet of the reactor cooler. For example, when the first outlet of the reactor and the second inlet of the reactor cooler are connected by a pipe section, the pipe section may include an apparatus that generates bubbles of carbon monoxide in the pipe section as the first stream traverses the pipe section. The carbon monoxide bubbles may serve as a reservoir to replenish the carbon monoxide that is depleted from the reactor fluid due to a carbonylation reaction.

While a liquid is in a reactor cooler, the possibility of continuing reaction can cause depletion of carbon monoxide, which could result in catalyst loss via precipitation. Not wishing to be bound by any particular theory, it is believed that the third stream that includes carbon monoxide can eliminate or at least reduce the risk of catalyst precipitation. By contacting the first stream, the cooled reactor fluid, or a combination thereof with a third stream that includes carbon monoxide, the reactor cooler may serve as a secondary reactor, which may reduce the load to the primary reactor.

In some embodiments, the methods described herein include forwarding a second stream including the cooled reactor fluid to the reactor. The forwarding of the second stream including the cooled reactor fluid may be achieved by any known technique. In some embodiments, the first inlet of the reactor and the second outlet of the reactor cooler are connected by a pipe section, and the forwarding of the second stream to the reactor includes transporting the second stream through the pipe section.

Methyl Acetate Concentration

Generally, in the methods described herein, the reactor fluid has a first concentration of methyl acetate, the cooled reactor fluid has a second concentration of methyl acetate, and the second concentration is less than the first concentration. Therefore, at or upon exiting the first outlet of a reactor and before entering a second inlet of a reactor cooler, a first stream has the first concentration of methyl acetate, and at or upon exiting the second outlet of the reactor cooler and before entering the first inlet of a reactor, the cooled reactor fluid has the second concentration of methyl acetate. As a result, the first concentration and the second concentration may be determined by analyzing the first stream and the second stream, respectively, at the foregoing locations. Alternatively, the first concentration and the second concentration may be determined by analyzing the reactor fluid in the reactor or the cooled reactor fluid in the reactor cooler, respectively.

In some embodiments, the second concentration of methyl acetate is about 10% to about 40% less than the first concentration of methyl acetate. In other words, if the first concentration of methyl acetate is 10% by weight of the reactor fluid, then the second concentration of methyl acetate would be about 6% (i.e., about 40% less than the first concentration) to about 9% (i.e., about 10% less than the first concentration) by weight of the reactor fluid. In some embodiments, the second concentration of methyl acetate is about 20% to about 40% less than the first concentration of methyl acetate. In some embodiments, the second concentration of methyl acetate is about 20% to about 30% less than the first concentration of methyl acetate.

In some embodiments, the first concentration of methyl acetate is about 2.7% to about 3.3% by weight based on the weight of the reactor fluid, and the second concentration of methyl acetate is about 2% to about 2.4% by weight based on the weight of the cooled reactor fluid. As used herein, the phrases "based on the weight of the reactor fluid" and "based on the weight of the cooled reactor fluid" indicate that the weight percentages are based on the entire weight of the sample tested. The samples for measuring the first concentration may be drawn from the reactor fluid in a reactor or a first stream, and the samples for measuring a second concentration may be drawn from a cooled reactor fluid in a reactor cooler or a second stream.

In some embodiments, the first concentration of methyl acetate is about 2.8% to about 3.2% by weight based on the weight of the reactor fluid, and the second concentration of methyl acetate is about 2% to about 2.4% by weight based on the weight of the cooled reactor fluid. In some embodiments, the first concentration of methyl acetate is about 2.9% to about 3.1% by weight based on the weight of the reactor fluid, and the second concentration of methyl acetate is about 2% to about 2.4% by weight based on the weight of the cooled reactor fluid. In some embodiments, the first concentration of methyl acetate is about 2.8% to about 3.2% by weight based on the weight of the reactor fluid, and the second concentration of methyl acetate is about 2.1% to about 2.3% by weight based on the weight of the cooled reactor fluid.

Temperatures of Reactor and Reactor Cooler

Not wishing to be bound by any particular theory, it is believed that a desirable MeAc concentration reduction, as described herein, can be achieved, at least in part, by the temperature difference between the contents of the reactor and the contents of the reactor cooler (e.g., the temperature difference between (i) the first stream at or upon exiting the first outlet of a reactor and before the first stream enters the second inlet of a reactor cooler, and the (ii) the second stream at or upon existing the second outlet of a reactor cooler and before the second stream enters the first inlet of a reactor). Generally, the temperature of the contents of the reactor cooler (e.g., second stream) is less than the temperature of the contents of the reactor (e.g., first stream). If the temperature difference is not great enough, then the resulting insufficient heat removal may cause the reactor to overheat. If the temperature difference is too great, then the relatively slower reaction rate in the reactor cooler may not sufficiently reduce MeAc concentration in the reactor.

In some embodiments, a temperature of the second stream including the cooled reactor fluid is about 1.6° C. (3° F.) to about 13.9° C. (25° F.) less than a temperature of the first stream including the reactor fluid. In some embodiments, a temperature of the second stream including the cooled reactor fluid is about 2.7° C. (5° F.) to about 13.9° C. (25° F.) less than a temperature of the first stream including the reactor fluid. In some embodiments, a temperature of the second stream including the cooled reactor fluid is about 2.7° C. (5° F.) to about 11.1° C. (20° F.) less than a temperature of the first stream including the reactor fluid. In some embodiments, a temperature of the second stream including the cooled reactor fluid is about 5.5° C. (10° F.) to about 11.1° C. (20° F.) less than a temperature of the first stream including the reactor fluid. In some embodiments, a temperature of the second stream including the cooled reactor fluid is about 8.3° C. (15° F.) to about 11.1° C. (20° F.) less than a temperature of the first stream including the reactor fluid. In some embodiments, a temperature of the second stream including the cooled reactor fluid is about 11.1° C. (20° F.) less than a temperature of the first stream including the reactor fluid.

In some embodiments, a temperature of the second stream including the cooled reactor fluid is about 176° C. (350° F.) to about 182.2° C. (360° F.), and a temperature of the first stream including the reactor fluid is about 187° C. (370° F.) to about 193.3° C. (380° F.). In some embodiments, a temperature of the second stream including the cooled reactor fluid is about 177.8° C. (352° F.) to about 181.1° C. (358° F.), and a temperature of the first stream including the reactor fluid is about 189° C. (372° F.) to about 192.2° C. (378° F.). In some embodiments, a temperature of the second stream including the cooled reactor fluid is about 178° C. (354° F.) to about 180° C. (356° F.), and a temperature of the first stream including the reactor fluid is about 190° C. (374° F.) to about 191.1° C. (376° F.). In some embodiments, a temperature of the second stream including the cooled reactor fluid is about 179.4° C. (355° F.), and a temperature of the first stream including the reactor fluid is about 187° C. (370° F.) to about 190.6° C. (375° F.).

Generally, the residence time of a first stream that includes the reactor fluid in a reactor is greater than its residence time in a reactor cooler. The residence times may be adjusted in view of any one of more factors, including, but not limited to, a desired concentration of methyl acetate in the reactor fluid, the amount of additional carbon monoxide provided as a third stream, the rate of carbonylation reaction in the reactor cooler, the temperature difference between the contents of the reactor and the contents of the reactor cooler, or a combination thereof.

In some embodiments, a residence time of the first stream including the reactor fluid in the reactor cooler is about 50% to about 99% less than a residence time of the reactor fluid in the reactor. In some embodiments, a residence time of the first stream including the reactor fluid in the reactor cooler is about 60% to about 99% less than a residence time of the reactor fluid in the reactor. In some embodiments, a residence time of the first stream including the reactor fluid in the reactor cooler is about 70% to about 99% less than a residence time of the reactor fluid in the reactor. In some embodiments, a residence time of the first stream including the reactor fluid in the reactor cooler is about 80% to about 99% less than a residence time of the reactor fluid in the reactor. In some embodiments, a residence time of the first stream including the reactor fluid in the reactor cooler is about 80% to about 95% less than a residence time of the reactor fluid in the reactor. In some embodiments, a residence time of the first stream including the reactor fluid in the reactor cooler is about 90% to about 95% less than a residence time of the reactor fluid in the reactor.

In some embodiments, a residence time of the first stream including the reactor fluid in the reactor cooler is about 1 minute to about 3 minutes, and the residence time of the reactor fluid in the reactor is about 15 minutes to about 19 minutes.

In some embodiments, the methods described herein also include recovering as steam a portion of waste heat from the reactor cooler. The waste heat from the reactor cooler can be recovered as steam that can be used in purification train reboilers or other process heaters. In some embodiments, about 50% to about 80% of the processes' heating requirements can be satisfied by this step, thereby eliminating, or reducing, the reliance on independent steam generation.

The reactor cooler generally may have one or more features of coolers known in the art. In some embodiments, the reactor cooler includes a shell and tube heat exchanger. In some embodiments, a cooling fluid, such as water, is passed through the shell or the tubes of the reactor cooler, and the first stream/cooled reactor fluid is passed through the tubes or the shell, respectively.

The reactor fluid also may include a soluble catalyst system. The soluble catalyst system may include a catalyst and methyl iodide. The catalyst generally may include any carbonylation catalyst. In some embodiments, the catalyst is a rhodium catalyst. In some embodiments, the catalyst is an iridium catalyst.

In some embodiments, methyl iodide acts as a catalyst promoter. The concentration of methyl iodide may be from about 0.6 wt. % to about 36 wt. % based on the total weight of the reactor fluid. Alternatively or additionally, methyl iodide can be generated in the reactor by adding hydrogen iodide.

Suitable rhodium catalysts are described, for example, in U.S. Pat. No. 5,817,869, which is incorporated herein by reference. Suitable rhodium catalysts include rhodium metal and rhodium compounds. Preferably, the rhodium compounds are selected from the group consisting of rhodium salts, rhodium oxides, rhodium acetates, organo-rhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. Most preferably, the rhodium compounds are selected from the group consisting of $[H]Rh(CO)_2I_2$, $Rh(CH_3CO_2)_2$, the like, and mixtures thereof.

Suitable iridium catalysts are described, for example, in U.S. Pat. No. 5,932,764, which is incorporated herein by reference. Suitable iridium catalysts include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3 \times 4H_2O$, $IrBr_3 \times 4H_2O$, $Ir_3(CO)_{12}$, $Ir_2O_3$, $IrO_2$, $Ir(acac)(CO)_2$, $Ir(acac)_3$, $Ir(OAc)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates.

The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are acetates.

In some embodiments, the reactor fluid further comprises a phosphine oxide, such as a pentavalent alkyl phosphine oxide. Examples of suitable phosphine oxides are described at U.S. Pat. No. 9,790,159, which is incorporated herein by reference.

In some embodiments, the phosphine oxides are represented by the formula $R_3PO$, wherein R is alkyl or aryl, O is oxygen, P is phosphorous. In some embodiments, the phosphine oxides include a compound mixture of at least four phosphine oxides, wherein each phosphine oxide has the formula $OPX_3$, wherein O is oxygen, P is phosphorous and X is independently selected from $C_4$-$C_{18}$ alkyls, $C_4$-$C_{18}$ aryls, $C_4$-$C_{18}$ cyclic alkyls, $C_4$-$C_{18}$ cyclic aryls and combinations thereof. Each phosphine oxide has at least 15, or at least 18 total carbon atoms.

Examples of suitable phosphine oxides for use alone or in the compound mixture include, but are not limited to, tri-n-hexylphosphine oxide (THPO), tri-n-octylphosphine oxide (TOPO), tris(2,4,4-trimethylpentyl)-phosphine oxide, tricyclohexylphosphine oxide, tri-n-dodecylphosphine oxide, tri-n-octadecylphosphine oxide, tris(2-ethylhexyl) phosphine oxide, di-n-octylethylphosphine oxide, di-n-hexylisobutylphosphine oxide, octyldiisobutylphosphine oxide, tribenzylphosphine oxide, di-n-hexylbenzylphosphine oxide, di-n-octylbenzylphosphine oxide, 9-octyl-9-phosphabicyclo[3.3.1]nonane-9-oxide, dihexylmonooctylphosphine oxide, dioctylmonohexylphosphine oxide, dihexylmonodecylphosphine oxide, didecylmonohexylphosphine oxide, dioctylmonodecylphosphine oxide, didecylmonooctylphosphine oxide, and dihexylmonobutylphosphine oxide and the like.

The compound mixture of phosphine oxides may include from 1 wt. % to 60 wt. %, or from 35 wt. % to 50 wt. % of each phosphine oxide based on the total weight of compound mixture. In some embodiments, the compound mixture includes TOPO, THPO, dihexylmonooctylphosphine oxide and dioctylmonohexylphosphine oxide. For example, the compound mixture may include from 40 wt. % to 44 wt. % dioctylmonohexylphosphine oxide, from 28 wt. % to 32 wt. % dihexylmonooctylphosphine oxide, from 8 wt. % to 16 wt. % THPO and from 12 wt. % to 16 wt. % TOPO, for example.

Figure 2:
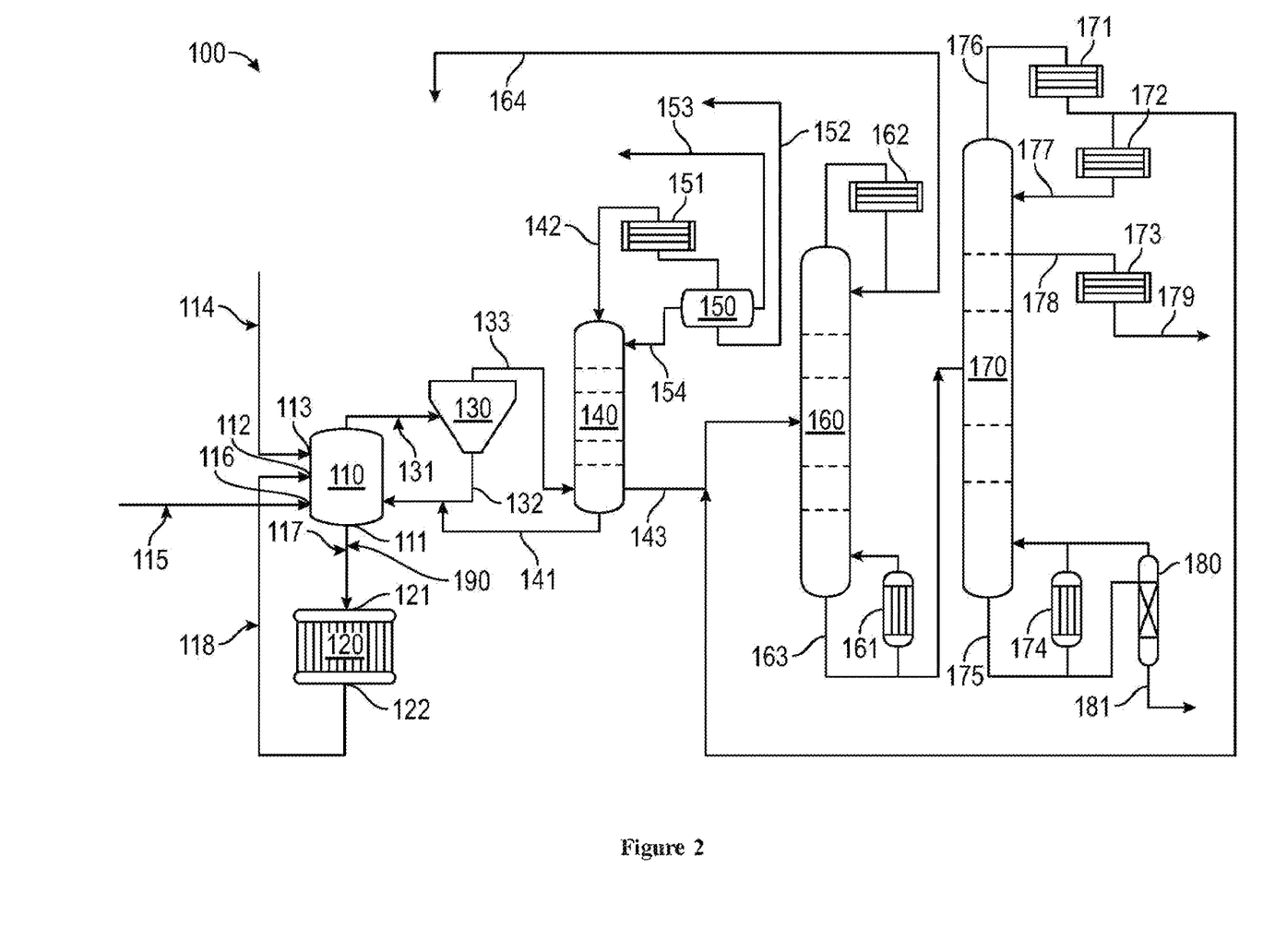
FIG. 2 depicts an embodiment of a system that may be used to perform an embodiment of a method described herein.

One embodiment of a system in which the methods described herein may be performed is depicted at FIG. 2. The system 100 of FIG. 2 includes a reactor 110 including a first outlet 111 and a first inlet 112 through which fluids are forwarded to and returned from, respectively, a reactor cooler 120 which includes a corresponding second inlet 121 and second outlet 122. The system also includes a flash tank 130, a light ends column 140, a decanter 150, a drying column 160, a heavy ends column 170, and a waste aid stripper 180. The system also includes various coolers and subcoolers (151, 161, 162, 171, 172, 173, 174).

Embodiments of the methods described herein may be performed in the system depicted at FIG. 2. In some embodiments, a feed 114 including MeOH and optionally co-fed MeAc enters directly into the reactor 110 via an inlet 113 without special distribution, and a feed 115 including CO enters through a sparger ring 116 near the bottom of the reactor 110.

In some embodiments, one or more other streams are also fed to the reactor 110. These streams may include at least one of the following recycle-streams: (1) a catalyst recycle stream 132 from the flash tank 130, (2) a heavy phase liquid stream 152 from the light ends column decanter 150, (3) a light phase liquid stream 153 from the light ends column decanter 150, and (4) a dilute acid stream 164 from the drying column 160 overhead. One or more of stream 152, stream 153, and stream 164 may be combined with the methanol feed 114 before entering the reactor 110.

Disposed in the reactor 110, in some embodiments, is a soluble catalyst system, which may include rhodium (the catalyst) and methyl iodide-hydrogen iodide (the promoter, MeI—HI). The soluble catalyst system may cause the reaction to occur at a reasonable rate. In some embodiments, methanol converts to MeAc practically instantly in the reactor 110.

An additive that may include a pentavalent alkyl phosphine oxides also may be disposed in the reactor 110, and the additive may provide increased catalyst stability against precipitation in the flash tank and/or allow increased catalyst activity while lowering the water required in the reactor.

In some embodiments, total reactor pressure in the reactor 110 is controlled by CO make up and is maintained at a pressure as described herein.

In some embodiments, HOAc produced in the reactor 110 is removed by adiabatically flashing the reactor fluid 131 at low pressure to a flash tank 130. The cooled liquid 132 from the flash tank 130 (which, in some embodiments, is about 262° F., and includes a homogeneous catalyst system) may be returned to the reactor 110 while a vaporized product overhead stream 133 may be sent to a light ends column 140. The bottoms stream 141 from the light ends column 140 may be returned to the reactor 110. In some embodiments, this flash cooled liquid flash tank recycle stream includes a, if not the, primary source of cooling to remove heat produced by the catalyzed carbonylation of MeOH. Additional cooling is provided by recirculating reactor fluid through the reactant cooler 120.

In some embodiments, the vaporized overhead stream 133 from the flash tank 130 contains acetic acid, MeI, $H_2O$, MeAc, and trace quantities of CO and HI. This vapor stream 133 may be fed to the lower portion of the light ends column (LEC) 140. In this column 140, a concentrated acetic acid stream may be recovered as a side draw 143 that also contains water, methyl iodide, methyl acetate, and trace quantities of hydrogen iodide. This stream 143 may be fed to the drying column (DC) 160. In some embodiments, the LEC bottoms stream 141 is not controlled and drains back to the flash tank 130. The overhead lights stream 142 may be cooled by a cooler 151 and fed to the decanter 150, which, in some embodiments, achieves a phasing out of a predominantly MeI containing heavy phase 152 and an aqueous light phase 153. In some embodiments, level controlled heavy phase recycle is used to maintain reactor MeI concentration. A portion of decanter light phase 154 may provide reflux to the LEC 140 with the remainder of the light phase 153 being recycled to the reactor 110.

In some embodiments, the DC 160 removes $H_2O$ from the LEC 160 acetic side draw 143. The DC bottoms 163 (which may include dry acetic acid) may feed the heavy ends column (HEC) 170. The HEC 170 may remove ppm quantities of propionic acid from acetic acid. Also, high boiling impurities may be removed through the bottom of the column 170. The HEC bottoms 175 may be separated in the Waste Acid Stripper (WAS) 180, where iodides, propionic acid, and other impurities are removed in a bottoms purge 181, and acetic acid may be recovered from a top stream 176 in the overhead cooler 171 and reflux cooler 172 and the stream 177 is recycled back to the HEC 170. Product acetic acid 179 may result from a side draw 178 near the top of the HEC 170 that is passed through a cooler 173.

In some embodiments, the amount of water necessary for stable operation of the methods described herein the system 100 of FIG. 2 is less than 5%, due, at least in part, to the additive that includes a pentavalent alkyl phosphine oxides. This may allow a reduction of the acetic acid recycle 132 from the purification train. The acetic acid recycle reduction may allow, in turn, an increase in capacity. The capacity increase may be greater than 5%, and as high as 30-50% with little or no modification of the existing purification section (140, 150, 160, 170, 180) of the system of FIG. 2.

To eliminate or reduce the one or more problems associated with the heat surplus and/or high MeAc, the contents of the reactor 110 are circulated to the reactor cooler 120, which in some embodiments, removes or reduces the heat generated by the cumulative effects of acetic acid recycle reduction and production increase. In some embodiments, the reactor cooler 120 of the system 100 of FIG. 2, is about 2 to about 10 times larger than existing process coolers used in known methods.

In some embodiments, a stream 117 of reactor fluid is withdrawn from the reactor 110 at the reactor temperature and fed to the reactor cooler 120, where a portion of the heat of the reactor fluid is removed before the stream 118 is returned to the reactor 110 at a lower temperature. The reactor fluid is saturated with CO. In some embodiments, the reactor cooler 120 operates at a lower temperature than the reactor 110 itself, but the temperature of the reactor cooler 120 is high enough to allow a carbonylation reaction to continue, albeit at a reduced rate. Not wishing to be bound by any particular theory, this may have a beneficial effect of reducing the MeAc concentration from the feed 117 to the exit of the reactor cooler 122, which in turn can reduce the MeAc concentration in the reactor 110, and allow stable operation of the reactor 110 and the decanter 150. Therefore, in some embodiments, the reactor cooler 120 may be configured to operate at a temperature window that permits it to serve as a heat exchanger reactor.

Continuing depletion of CO reactant due the increased residence time in the reactor cooler 120 can lead to undesirably low CO concentration which, in turn, can destabilize a catalyst, such as a Rh catalyst, thereby increasing the likelihood that the catalyst will precipitate out of solution. Therefore, in some embodiments, the methods herein include contacting the stream 117 of reactor fluid with a CO feed 190 after the stream 117 exits the reactor 110, but before the steam 117 enters the reactor cooler 120. The CO feed 190 may include bubbles of CO that contact the stream 117. Alternatively, the stream 117 may be contacted with CO while inside the reactor cooler 120.

In some embodiments, the reactor cooler 120 is a shell and tube heat exchanger. In some embodiments, the stream 117 of reactor fluid is fed to the reactor cooler 120 and a coolant like water or other suitable heat removal liquid is used to remove heat from the stream 117.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Comparative Example 1—Impact of Increased MeAc Concentration

Comparative Example 1 was conducted in a GAA reactor system similar to that shown in FIG. 2 but without reactor cooler 120 and accompanying components: outlet 111, inlet 112, streams 117, 118 or CO feed 190. This example demonstrated how increased MeAc concentration may cause reduced density of the heavy phase in the decanter 150.

The data of Table 1 were obtained from a continuous methanol carbonylation process equipped with (i) a reactor Raman analyzer capable of continuously quantifying methyl acetate concentration, and (ii) a decanter heavy phase on-line densitometer capable of continuously quantifying density.

TABLE 1

| Time (hours) | Heavy Phase Density, g/mL | Reactor MeAc, wt % |
|---|---|---|
| 0 | 1.756 | 3.03 |
| 1 | 1.746 | 3.12 |

TABLE 1-continued

| Time (hours) | Heavy Phase Density, g/mL | Reactor MeAc, wt % |
|---|---|---|
| 2.4 | 1.741 | 3.41 |
| 3.6 | 1.736 | 3.79 |
| 6.5 | 1.721 | 3.93 |
| 7.7 | 1.729 | 3.73 |
| 11 | 1.752 | 2.85 |

A target steady state reactor methyl acetate concentration of 3 wt % was exceeded when the heavy phase recycle flow rate to reactor was unintentionally decreased, which leads to a decrease in reaction rate and a buildup of methyl acetate.

The table shows the undesired decrease in heavy phase density accompanying the increase in reactor methyl acetate concentration.

This example demonstrated the undesired effect of increasing reactor methyl acetate concentration on decanter heavy phase density. While increasing the reactor temperature, increasing the catalyst concentration, and/or decreasing the feed rate can decrease methyl acetate concentration, each of these adjustments is accompanied by one or more undesirable outcomes, including, but not limited to, an energy cost, a material cost, and/or a production decrease.

Example 1—Effects of Dual Purpose Reactor Cooler

The GAA reactor system of FIG. 2 was used in this example. The reactor and reactor cooler operating parameters are summarized as Table 2.

The extent of continuing reaction (MeAc and CO consumption & GAA formation) in the reactor cooler was controlled by adjusting the reactor cooler temperature. The data of Table 2 indicated that the space time yield (STY) in the reactor cooler was approximately half of the reactor STY at the temperatures indicated at Table 2.

Based on reactor cooler inlet composition (substantially reactor composition), STY, and residence time, reactor cooler outlet compositions were analyzed, as depicted at Table 3. It should be noted that as MeAc was only partially consumed in the reactant cooler, iodide equilibrium was unaffected and the MeI/HI ratio remained relatively constant.

TABLE 2

| Variable | Reactor | Rx Cooler |
|---|---|---|
| Temp, ° C. | 190.6 | 179.4 |
| Approximate STY | 10 | 5 |
| Residence Time, mins. | 17 | 1.35 |
| Liquid Volume, liters | 56,781.2 | 5,212.5 |

TABLE 3

| Component | Rx Cooler Inlet, wt % | Rx Cooler Outlet, wt % |
|---|---|---|
| $H_2O$ | 6 | 5.8 |
| MeAc | 3 | 2.2 |
| MeI | 14 | 14 |
| HI | 5 | 5 |
| R3PO | 7 | 7 |
| Rh | 700 PPM | 700 PPM |
| Acetic acid | 65 | 65 |

In this example, there were 12 reactor cooler turnovers per reactor turnover. Taking this turnover ratio into account along with the relative volumes of the reactor and reactor cooler, the expected changes in steady state reactor MeAc concentration when the cooler was in operation (under the conditions shown at Table 2) were calculated and are shown at Table 4. The data suggest that, at steady state behavior, a reactor MeAc concentration of 3.0 wt % without the reactor cooler in operation would be lowered to 2.45 wt % with the reactor cooler on-line.

TABLE 4

| Cooler Pass# | Concentration (wt %) MeAc (Bef. Cooler Pass) | Concentration (wt %) MeAc (Aft. Cooler Pass) |
| --- | --- | --- |
| 1 | 3.00 | 2.93 |
| 2 | 2.93 | 2.86 |
| 3 | 2.86 | 2.80 |
| 4 | 2.80 | 2.74 |
| 5 | 2.74 | 2.69 |
| 6 | 2.69 | 2.65 |
| 7 | 2.65 | 2.61 |
| 8 | 2.61 | 2.57 |
| 9 | 2.57 | 2.54 |
| 10 | 2.54 | 2.51 |
| 11 | 2.51 | 2.48 |
| 12 | 2.48 | 2.45 |

There was some exothermicity associated with the ongoing carbonylation reaction in the reactor cooler which countered the desired cooling effect, but this was fairly modest and the reactant cooler's cooling capacity compensated for this effect.

By significantly increasing cooling capacity with recirculating coolers, the amount of flash and recycle of acid is reduced, thus unloading the back-end purification. The flow reduction to the backend purification allows a higher production rate to be achieved with essentially the same equipment.

Example 2

Figure 3:
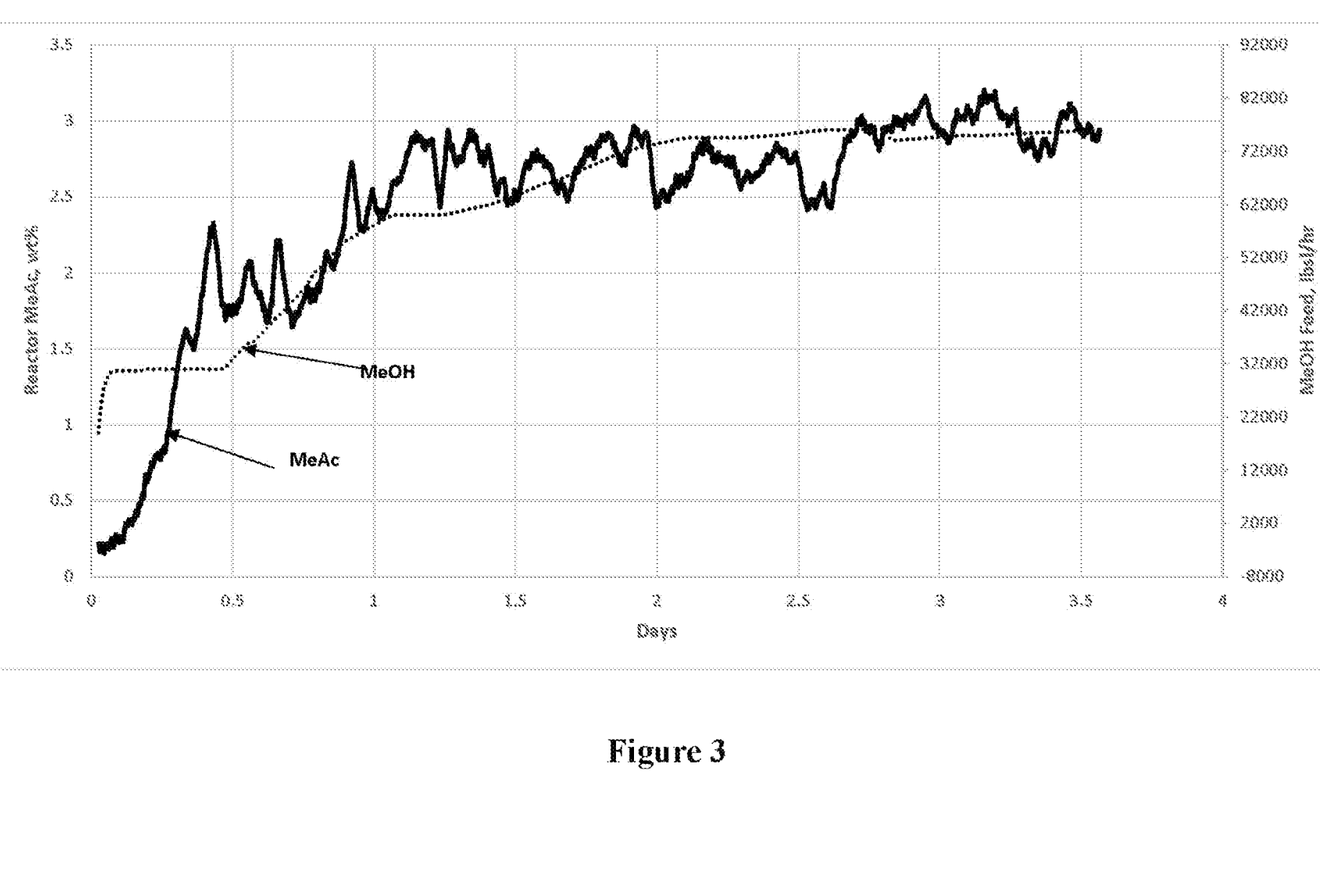
FIG. 3 is a graph presenting data from a continuous methanol carbonylation unit.

As described above, decreasing the feed rate can decrease methyl acetate concentration. By corollary, increasing the feed rate will increase methyl acetate concentration. FIG. 3 presents start-up data collected over a 3.5 day period of a continuous methanol carbonylation unit without reactor cooler in operation, e.g., using the system of Comparative Example 1. As shown, the target steady state MeAc concentration of about 3 wt % was obtained at the conclusion of the methanol feed ramp. In this case, the Rh catalyst concentration was increased to keep MeAc concentration at or below 3 wt %.

Figure 4:
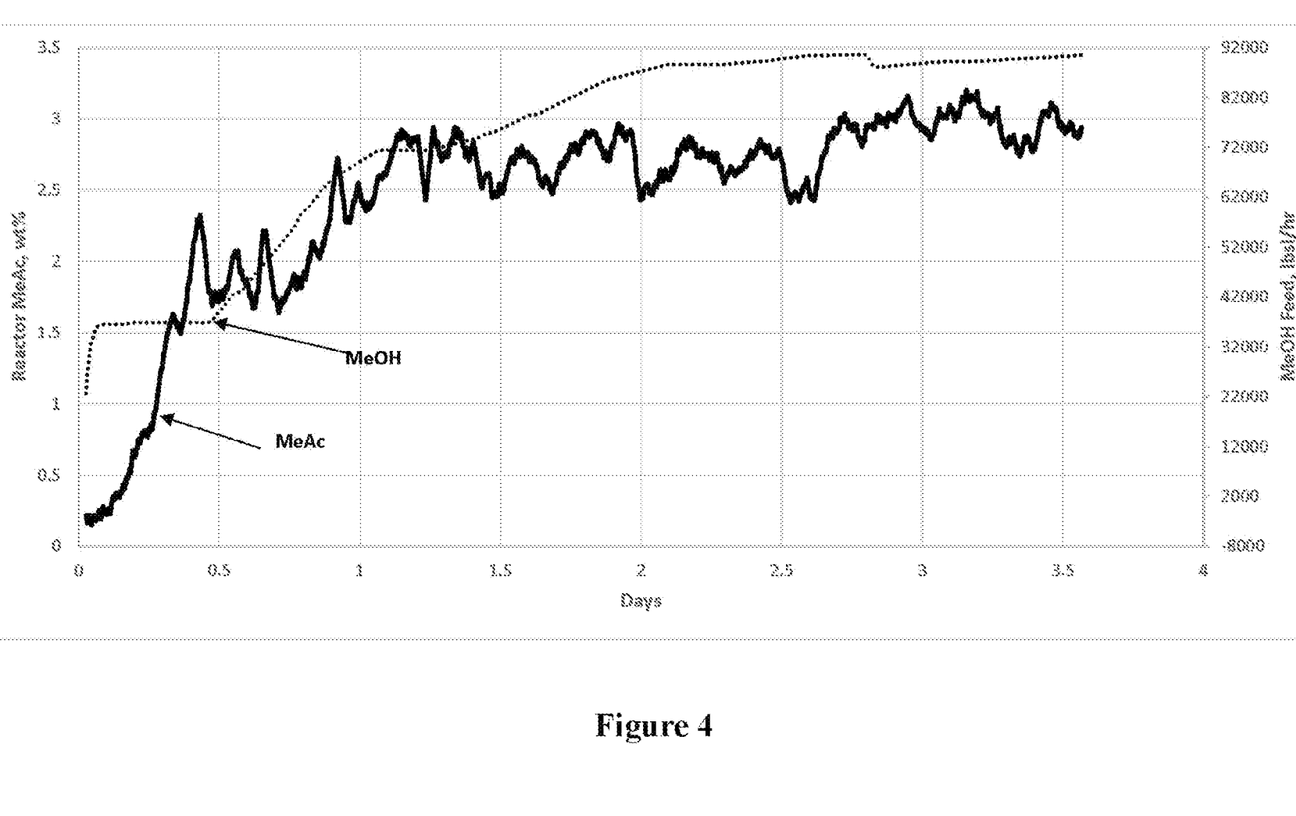
FIG. 4 presents simulated data from a continuous methanol carbonylation unit in accordance with an embodiment described herein.

FIG. 4 represents a simulated condition where a similar steady state methyl acetate concentration is maintained but now at a favorably higher feed rate and, by corollary, higher production rate. This condition can be reached by an increase in Rh catalyst concentration, an increase in reactor temperature, an increase in methyl iodide promoter concentration or by bringing the reactor cooler on-line under the operational conditions as shown in the data in Tables 2-4.

Those skilled in the art of methanol carbonylation will recognize that Rh catalyst is extraordinarily expensive and that the extra expense involved in increasing the Rh concentration to allow a higher feed rate is associated not only with the initial additional cost but also with higher ongoing usage costs due to increased losses from entrainment at the higher stream velocities associated with higher feed and production rates. Increasing the reactor temperature has a major limitation associated with a corresponding increase in corrosion rates and as such, is not a variable that can be typically employed. Increasing the volatile methyl iodide promoter concentration in the reactor will lead to increased methyl iodide concentration and thus, lower acetic acid concentration, in the flash overhead which will unfavorably offset some of the increased production gained by feed rate increase. Furthermore, higher reactor methyl iodide concentration, due to its volatility and high vapor pressure, will lead to an unfavorable decrease in CO partial pressure.

In contrast, the reactor cooler option allows a higher methanol feed rate while maintaining a steady state methyl acetate concentration associated with a lower methanol feed rate, i.e., using the GAA reactor system of FIG. 2. This helps ensure that the heavy phase recycle flow rate from the decanter to the reactor is maintained and the decrease in reaction rate accompanying a decrease in heavy phase recycle flow rate is avoided. The benefits of the reactor cooler can be achieved without any of the foregoing limitations or constraints.

The particular embodiments disclosed above are merely illustrative, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is present, or alternatively, the element is not present, both alternatives being within the scope of the claim. In the claims, means-plus-function clauses are intended to cover the structures described herein as performing the recited function and not only structural equivalents, but also equivalent structures. It is the express intention of the applicant not to invoke 35 U.S.C. § 112, paragraph 6 for any limitations of any of the claims herein, except for those in which the claim expressly uses the words "means for" together with an associated function.

Numbers and ranges disclosed above may vary by some amount. Whenever a numerical range with a lower limit and an upper limit is disclosed, any number and any included range falling within the range is specifically disclosed. In particular, each range of values (of the form, "from about a to about b," or, equivalently, "from approximately a to b," or, equivalently, "from approximately a-b") disclosed herein is to be understood to set forth each number and range encompassed within the broader range of values. Also, the terms in the claims have their plain, ordinary meaning unless otherwise explicitly and unambiguously defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Accordingly, the scope of protection is not limited by the description set out above but is only limited by the claims which follow, such scope including equivalents of the subject matter of the claims.

We claim:

1. A method for producing acetic acid, the method comprising:
   contacting a first amount of carbon monoxide with a reactor fluid, in a reactor, in the presence of a carbonylation catalyst, the reactor fluid comprising iodide, less than or equal to 6 wt % water based on the total weight of the reactor fluid, and one or more additives, in-situ generated derivatives of the one or more additives, or combinations thereof at an additive to iodide molar ratio of 0.5:1 to 5:1, under carbonylation conditions sufficient to form acetic acid and an intermediate reaction product comprising methyl acetate, the reactor fluid having a first concentration of methyl acetate, wherein the one or more additives comprise a compound mixture of tri-n-octylphosphine oxide (TOPO), tri-n-hexylphosphine oxide (THPO), dihexylmonooctylphosphine oxide and dioctylmonohexylphosphine oxide;
   directing a first stream comprising a portion of the reactor fluid from the reactor to a reactor cooler, the first stream having a first concentration of methyl acetate;
   cooling the portion of the reactor fluid received in the reactor cooler for a residence time sufficient to form a cooled reactor fluid having a second concentration of methyl acetate less than the first concentration of methyl acetate;
   directing a second stream comprising the cooled reactor fluid from the reactor cooler to the reactor;
   contacting a third stream comprising a second amount of carbon monoxide with at least one of the first stream and the reactor fluid received in the reactor cooler;
   maintaining an acetic acid evaporation rate in the reactor; and
   recovering acetic acid.

2. The method of claim 1, wherein the second concentration of methyl acetate is about 10% to about 40% less than the first concentration of methyl acetate.

3. The method of claim 1, wherein the second concentration of methyl acetate is about 20% to about 40% less than the first concentration of methyl acetate.

4. The method of claim 1, wherein the second concentration of methyl acetate is about 20% to about 30% less than the first concentration of methyl acetate.

5. The method of claim 1, wherein the first concentration of methyl acetate is about 2.7% to about 3.3% by weight based on the weight of the reactor fluid, and the second concentration of methyl acetate is about 2% to about 2.4% by weight based on the weight of the cooled reactor fluid.

6. The method of claim 1, wherein the first concentration of methyl acetate is about 2.9% to about 3.1% by weight based on the weight of the reactor fluid, and the second concentration of methyl acetate is about 2% to about 2.4% by weight based on the weight of the cooled reactor fluid.

7. The method of claim 1, wherein a temperature of the second stream comprising the cooled reactor fluid is about 1.6° C. to about 13.9° C. less than a temperature of the first stream comprising the reactor fluid.

8. The method of claim 1, wherein a temperature of the second stream comprising the cooled reactor fluid is about 2.7° C. to about 11.1° C. less than a temperature of the first stream comprising the reactor fluid.

9. The method of claim 1, wherein a temperature of the second stream comprising the cooled reactor fluid is about 176° C. to about 182.2° C., and a temperature of the first stream comprising the reactor fluid is about 187° C. to about 193.3° C.

10. The method of claim 1, wherein a temperature of the second stream comprising the cooled reactor fluid is about 179.4° C., and a temperature of the first stream comprising the reactor fluid is about 187° C. to about 190.6° C.

11. The method of claim 1, wherein the residence time of the first stream comprising the reactor fluid in the reactor cooler is about 70% to about 99% less than a residence time of the reactor fluid in the reactor.

12. The method of claim 1, wherein the residence time of the first stream comprising the reactor fluid in the reactor cooler is about 80% to about 95% less than a residence time of the reactor fluid in the reactor.

13. The method of claim 1, wherein the contacting of the first stream with the third stream comprises injecting the second amount of carbon monoxide into the reactor cooler through a sparger or supersonic injector.

14. The method of claim 1, wherein the contacting of the first stream with the third stream comprises generating bubbles of the second amount of carbon monoxide in an apparatus fluidly connecting the reactor and the reactor cooler.

15. The method of claim 1, further comprising recovering as steam a portion of waste heat from the reactor cooler.

16. The method of claim 1, wherein the reactor cooler comprises a shell and tube heat exchanger.

17. The method of claim 1, wherein the reactor fluid further comprises a soluble catalyst system, wherein the soluble catalyst system comprises a carbonylation catalyst and methyl iodide.

18. The method of claim 1, wherein the reactor fluid further comprises a pentavalent alkyl phosphine oxide.

19. The method of claim 1, further comprising applying with the first amount of carbon monoxide a pressure in the reactor of about 2.413 MPa to about 3.102 MPa.

20. The method of claim 1, further comprising applying with the first amount of carbon monoxide a pressure in the reactor of about 2.654 MPa to about 2.792 MPa.

* * * * *